United States Patent
Zhao

(10) Patent No.: US 12,275,883 B2
(45) Date of Patent: Apr. 15, 2025

(54) MULTIFUNCTIONAL ADDITIVE COMPOUNDS

(71) Applicant: Huntsman Petrochemical LLC, The Woodlands, TX (US)

(72) Inventor: Haibo Zhao, The Woodlands, TX (US)

(73) Assignee: HUNTSMAN PETROCHEMICAL LLC

( * ) Notice: Subject to any disclaimer, the term of this patent is extended or adjusted under 35 U.S.C. 154(b) by 869 days.

(21) Appl. No.: 17/427,946

(22) PCT Filed: Feb. 11, 2020

(86) PCT No.: PCT/US2020/017590
§ 371 (c)(1),
(2) Date: Aug. 3, 2021

(87) PCT Pub. No.: WO2020/172001
PCT Pub. Date: Aug. 27, 2020

(65) Prior Publication Data
US 2022/0025262 A1    Jan. 27, 2022

Related U.S. Application Data

(60) Provisional application No. 62/808,595, filed on Feb. 21, 2019.

(51) Int. Cl.
| | | |
|---|---|---|
| C09K 15/22 | (2006.01) | |
| A61K 8/86 | (2006.01) | |
| A61Q 19/00 | (2006.01) | |
| C08G 65/332 | (2006.01) | |
| C08G 65/333 | (2006.01) | |
| C10L 1/238 | (2006.01) | |
| C10L 1/2387 | (2006.01) | |
| C10L 10/04 | (2006.01) | |
| C10M 149/14 | (2006.01) | |
| C10N 30/00 | (2006.01) | |
| C10N 30/12 | (2006.01) | |

(52) U.S. Cl.
CPC .............. C09K 15/22 (2013.01); A61K 8/86 (2013.01); A61Q 19/00 (2013.01); C08G 65/3328 (2013.01); C08G 65/33303 (2013.01); C10L 1/238 (2013.01); C10L 1/2387 (2013.01); C10L 10/04 (2013.01); C10M 149/14 (2013.01); C10L 2200/0423 (2013.01); C10L 2230/085 (2013.01); C10M 2201/02 (2013.01); C10M 2217/04 (2013.01); C10M 2217/041 (2013.01); C10M 2217/06 (2013.01); C10N 2030/12 (2013.01); C10N 2030/24 (2020.05)

(58) Field of Classification Search
CPC .......... C08K 15/22; A61K 8/86; A61Q 19/00; C08G 65/3328; C08G 65/33303; C10L 1/238; C10L 10/04; C10L 2200/0423; C10L 2230/085; C10L 1/2387; C10M 149/14; C10M 2201/02; C10M 2217/04; C10M 2217/041; C10M 2217/06; C10N 2030/12; C10N 2030/24
See application file for complete search history.

(56) References Cited

U.S. PATENT DOCUMENTS

| | | |
|---|---|---|
| 3,773,479 A | 11/1973 | Dorn et al. |
| 3,894,849 A | 7/1975 | Polss |
| 4,144,034 A * | 3/1979 | Cummings ............. C10L 1/224 44/407 |
| 4,290,778 A | 9/1981 | Herbstman et al. |
| 4,332,737 A | 6/1982 | Manos |
| 4,419,105 A | 12/1983 | Sung |
| 4,536,189 A | 8/1985 | Sung |
| 4,631,069 A | 12/1986 | Sung |
| 4,659,337 A | 4/1987 | Sung |
| 4,689,051 A | 8/1987 | Sung |
| 4,834,897 A * | 5/1989 | Sung .................... C10M 133/06 508/281 |
| 4,865,621 A | 9/1989 | Sung |
| 5,064,571 A | 11/1991 | Speranza et al. |
| 5,705,603 A | 1/1998 | Krull et al. |
| 10,131,859 B2 | 11/2018 | Wolf et al. |
| 2011/0138683 A1 | 6/2011 | Altamirano et al. |

FOREIGN PATENT DOCUMENTS

| | | |
|---|---|---|
| GB | 2017145 A | 10/1979 |
| WO | 1999/59958 | 11/1999 |
| WO | 2016/153913 | 9/2016 |

OTHER PUBLICATIONS

Brazilian Preliminary Office Action issued Nov. 7, 2023, in corresponding Brazilian Application No. BR 11 2021 016177 5 (English translation enclosed herewith).

International Search Report and Written Opinion received in corresponding PCT Application PCT/US2020/017590 completed Apr. 4, 2020 and mailed Jun. 16, 2020.

* cited by examiner

Primary Examiner — Rabon A Sergent
(74) Attorney, Agent, or Firm — HUNTSMAN PETROCHEMICAL LLC; Aleece Hayes

(57) ABSTRACT

The present disclosure generally relates to a multifunctional additive obtained from the reaction of: (a) an intermediate obtained from the reaction of maleic anhydride and a polyoxyalkylene monoamine; and (b) an amine compound comprising a primary amine group and/or a secondary amine group and its use in a variety of applications, including, but not limited to: as a corrosion inhibitor or friction modifier in aqueous and non-aqueous systems; in fuel deposit control agents; as a dispersant in pigment, asphalt and cement compositions; and as a detergent.

13 Claims, No Drawings

MULTIFUNCTIONAL ADDITIVE COMPOUNDS

CROSS-REFERENCE TO RELATED APPLICATION

This application is the National Phase of International Application PCT/US2020/017590 filed Feb. 11, 2020 which claims the benefit of U.S. Provisional Patent Application Ser. No. 62/808,595, filed Feb. 21, 2019, the entire contents of which are expressly incorporated herein by reference.

STATEMENT REGARDING FEDERALLY SPONSORED RESEARCH OR DEVELOPMENT

Not applicable.

FIELD

The present disclosure generally relates to an additive compound obtained from the reaction of: (a) an intermediate obtained from the reaction of maleic anhydride and a polyoxyalkylene monoamine; and (b) an amine compound comprising a primary amine group and/or a secondary amine group. The additive is multifunctional and may be used in a variety of applications, including, but not limited to: as a corrosion inhibitor, detergent or friction modifier in aqueous and non-aqueous systems; as a dispersant in pigment, asphalt and cement compositions; and in fuel deposit control agents.

BACKGROUND

Corrosion of metal in the presence of water is a challenging and common problem in a variety of industries. Different types of metal corrosion are encountered, such as, for example, uniform corrosion over the entire metal surface and localized corrosion, such as pitting and crevice forming. Often, control of localized corrosion may be the critical factor in prolonging the useful life of the metal components in contact with water. Water containing significant concentrations (also referred to as "levels") of anions, such as chloride and sulfate, are prone to both uniform and localized corrosion. Uniform and localized corrosion often leads to the failure of the metallic components in contact with the water thus requiring replacement or extensive repairs and maintenance.

Alloy technology and galvanization have resulted in materials that can withstand some incidental contact with corrosive environments, but in a number of industrial applications (such as hydrocarbon exploration, recovery and refining, and chemical processing), more prolonged contact with corrosive environments often occurs. In particular, during the working life of an oil or gas well, various conduits and other components in the production zone can encounter considerable acidic corrosion. Corrosion inhibitors are therefore widely used in oil and gas production wells and pipelines to reduce corrosion of metal components and therefore prevent consequential production equipment failures.

Various types of corrosion inhibitors have been developed. For example, imidazolines have commonly been used as corrosion inhibitors and are viewed as the industry standard. However, imidazoline corrosion inhibitors are known to have poor aquatic toxicity. Non-imidazoline corrosion inhibitors include, for example:

U.S. Pat. No. 10,131,859 which discloses an acylated amine corrosion inhibitor formed from the reaction of a polyoxyalkylene monoamine and/or polyamine and a carboxylic acylating agent including fatty acids, isoaliphatic acids, dimer acids, addition dicarboxylic acids, trimer acids, addition tricarboxylic acids and hydrocarbyl substituted carboxylic acids;

US Pat. App. Publ. No. 2011/0138683 which discloses gemini surfactant corrosion inhibitors comprising bis-N-alkyl polyether, bis-N-alkenyl polyether, bis-N-cyclohexyl polyether, bis-N-aryl polyether bis-beta or alpha-imino acids or their salts; WO 1999/59958 which discloses a corrosion inhibitor formed by: (a) reacting an amino acid with an acyl halide to form an N-acylated amino acid product; (b) reacting the N-acylated amino acid of (a) with acetic anhydride or acetyl chloride; and (c) reacting the compound formed in (b) with an amine to form an N-acylated amino acid amide;

U.S. Pat. No. 5,064,571 which discloses a corrosion inhibitor formed from the reaction of fatty acids with polyoxyalkyleneamine residues;

U.S. Pat. No. 4,536,189 which discloses a corrosion inhibitor formed by: (a) reacting maleic anhydride with a hydrocarbon substituted mono primary etheramine; and (b) reacting the product formed in (a) with a heterocyclic nitrogen containing compound;

U.S. Pat. No. 4,419,105 which discloses a corrosion inhibitor formed from the reaction of maleic anhydride and a monofunctional polyetheramine;

U.S. Pat. No. 4,332,737 which discloses a corrosion inhibitor formed by: (a) reacting an alkylene polyamine containing at least 3 amino groups with an aliphatic monocarboxylic acid to form an amide; and (b) reacting the product formed in (a) with a dicarboxylic acid or acid anhydride;

U.S. Pat. No. 4,290,778 which discloses a corrosion inhibitor formed from the reaction of maleic anhydride with a hydrocarbyl alkoxy alkylene diamine;

U.S. Pat. No. 3,894,849 which discloses acylated alkylene polyamine corrosion inhibitors formed from the reaction of a polyamine and a monocarboxylic acid or an anhydride or acid halide of such monocarboxylic acid; and U.S. Pat. No. 3,773,479 which discloses a corrosion inhibitor formed from the reaction of maleic anhydride and a primary amine.

While state of the art corrosion inhibitors may be suitable for particular applications, a need exists for the development of alternative compounds that are capable of providing corrosion inhibition, as well as other performance characteristics, at low concentrations and do not introduce undesirable side effects into the system in which they are used.

SUMMARY

The present disclosure generally provides an additive compound obtained by the reaction of: (a) an intermediate formed from the reaction of a maleic anhydride and a polyoxyalkylene monoamine; and (b) an amine compound comprising a primary amine group and/or a secondary amine group.

In another embodiment, there is provided a composition including the additive compound of the present disclosure and at least one of a solvent, a surfactant or an auxiliary.

In still another embodiment, there is provided a corrosion inhibiting composition comprising the additive compound of the present disclosure and an aqueous fluid or a non-aqueous fluid.

DETAILED DESCRIPTION

The present disclosure is generally directed to an additive compound obtained by the reaction of: (a) an intermediate formed from the reaction of maleic anhydride and a polyoxyalkylene monoamine; and (b) an amine compound comprising a primary amine group and/or a secondary amine group.

The following terms shall have the following meanings:

The term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an amine" means one amine or more than one amine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same aspect. If the specification states a component or feature "may", "can", "could", or "might" be included or have a characteristic, that particular component or feature is not required to be included or have the characteristic.

The term "about" as used herein can allow for a degree of variability in a value or range, for example, it may be within 10%, within 5%, or within 1% of a stated value or of a stated limit of a range.

Values expressed in a range format should be interpreted in a flexible manner to include not only the numerical values explicitly recited as the limits of the range, but to also include all of the individual numerical values or sub-ranges encompassed within that range as if each numerical value and sub-range is explicitly recited. For example, a range such as from 1 to 6, should be considered to have specifically disclosed sub-ranges, such as, from 1 to 3, from 2 to 4, from 3 to 6, etc., as well as individual numbers within that range, for example, 1, 2, 3, 4, 5, and 6. This applies regardless of the breadth of the range.

The terms "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present disclosure.

The term "performance chemicals formulations" refers to non-personal care formulations that serve a broad variety of applications, and include non-limiting formulations such as, adhesives, agricultural, biocides, cement, coatings, electronics, fuels, household-industrial-institutional (HI&I), inks, membranes, metal working, paper, paints, pigments, plastics, printing, plasters, oil field, polyurethane, textile and wood-care formulations.

The term "personal care formulation" refers to such illustrative non-limiting formulations as skin, sun, oil, hair, cosmetic, and preservative formulations, including those to alter the color and appearance of the skin. Potential personal care formulations include, but are not limited to, polymers for increased flexibility in styling, durable styling, and increased humidity resistance for hair, skin, and color cosmetics, sun care water-proof/resistance, wear-resistance, and thermal protecting/enhancing formulations.

Where substituent groups are specified by their conventional chemical formula, written from left to right, they equally encompass the chemically identical substituents that would result from writing the structure from right to left, for example, —$CH_2O$— is equivalent to —$OCH_2$—.

The term "optional" or "optionally" means that the subsequently described event or circumstance may or may not occur, and that the description includes instances where said event or circumstance occurs and instances where it does not.

According to one embodiment, the additive compound may be obtained by the reaction of: (a) an intermediate formed from the reaction of maleic anhydride and a polyoxyalkylene monoamine; and (b) an amine compound comprising a primary amine group and/or a secondary amine group.

In one embodiment, the polyoxyalkylene monoamine which is reacted with maleic anhydride to form the intermediate (a) is a compound containing one amino group that is attached to the terminus of a polyether backbone. The amino group may be a primary (—$NH_2$) or a secondary (—NH—) amino group. In one embodiment, the amino group is a primary amino group. As further discussed below, the polyether backbone is based on, i.e., further defined by, alkylene oxide groups, such as propylene oxide (PO), ethylene oxide (EO), butylene oxide (BO) and mixtures thereof. In mixed structures, the ratios can be in any desired ratio and may be arranged in blocks (for e.g. repeating or alternating) or randomly distributed. In one non-limiting example, in a mixed EO/PO structure, the ratio of EO:PO can range from about 1:1 to about 1:50 and vice-versa. As such, the polyoxyalkylene monoamine may substantially define a polyethylene oxide, polypropylene oxide, and/or a polybutylene oxide. The molecular weights of the polyoxyalkylene monoamines can vary and may range up to a molecular weight of about 6,000.

Additionally, in some embodiments where the multifunctional additive of the present disclosure is prepared for use in highly polar systems, such as aqueous media, the polyoxyalkylene monoamine that is used in forming the intermediate (a) can include a sufficiently high fraction (e.g. a higher amount) of polar groups (i.e. polyethylene oxides) than apolar groups (i.e. polypropylene and/or butylene oxides) in order to achieve a level of water solubility sufficient for the particular area of use. For example, the polyoxyalkylene monoamine may contain greater than 50% by weight, or greater than 60% by weight, or greater than 75% by weight or greater than 90% by weight ethylene oxide. Similarly, in the case of forming dispersants for use in non-polar systems, the polyoxyalkylene monoamine can include a sufficiently high fraction (e.g. a higher amount) of apolar groups than polar groups, such as greater than 50% by weight or greater than 60% by weight or greater than 75% by weight or greater than 90% by weight of propylene oxide and/or butylene oxide. In the case of forming multifunctional additives for use in systems where broad compatibility is important, the polyoxyalkylene monoamine can include a balanced combination of such polar and apolar groups.

The polyoxyalkylene monoamine may generally be prepared by reaction of a monohydric initiator, for e.g. an alcohol, with ethylene and/or propylene oxide and/or butylene oxide. This reaction is followed by conversion of the resulting terminal hydroxyl group to an amine, thereby providing a polyether backbone which includes propylene oxide (PO), ethylene oxide (EO), butylene oxide (BO) or mixtures thereof, and a terminal amino group, for e.g., a terminal primary amino group or a terminal secondary amino group, preferably a primary amino group. According to one embodiment, the alcohol may be an aliphatic having 1-35 carbon atoms or aromatic alcohol having from 6-35 carbon atoms, both of which may be further substituted with moieties such as alkyl, aryl, arylalkyl and alkaryl substituents. In another embodiment, the alcohol is an alkanol having 1-18 carbon atoms, or 1-10 carbon atoms, such as lower alkyl derived alkanols including for example, methanol, ethanol, propanol, butanol, isopropanol, sec-butanol and the like. In another embodiment, the alcohol may be an alkylphenol where the alkyl substituent is a straight or branched chain alkyl of from 1-24 carbon atoms such as from 4-16 carbon atoms, or an aryl substituted phenol including mono- di- and tri-phenyl-phenol, or an alkaryl phenol, or an arylalkylphenol such as tri-strylphenol, or naphthol, or an alkyl substituted naphthol.

According to one particular embodiment, the polyoxyalkylene monoamine is a compound having a formula:

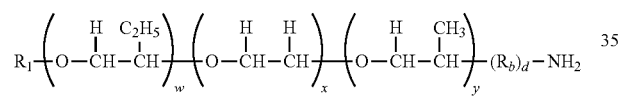

where $R_1$ is hydrogen, a $C_1$ to $C_{20}$ alkyl group or a $C_6$ aryl group optionally substituted with one or more $C_1$ to $C_{10}$ alkyl groups; w, x, and y are each independently an integer between zero to about 100, subject to the proviso that w+x+y is greater than two; d is 0 or 1; and, $R_b$ is a $C_1$ to $C_{10}$ alkyl group. In some embodiments, w, x and y may be an integer zero to about 50, or zero to about 20, or zero to about 10, subject to the proviso that w+x+y is greater than two.

The above structure may include homopolymers and co-polymers of any one or more of the following, either alone or mixed with one another in any proportion: ethylene oxide, propylene oxide, and butylene oxide. According to one aspect, the molecular weight of the polyoxyalkylene monoamine may be any molecular weight between about 500 and about 6000. In another particular embodiment, the polyoxyalkylene monoamine may have a molecular weight between about 600 and about 3000. In still another particular embodiment, the polyoxyalkylene monoamine may have a molecular weight of at least 1000, or at least 2000, or at least 3000, or at least 4000 or even at least 5000.

Examples of polyoxyalkylene monoamines of the above structure include, without limitation, those available from Huntsman Petrochemical LLC under the trademarks JEFFAMINE® amines and SURFONAMINE® amines, as well as analogous compounds offered by other companies comprising polyoxyalkylene primary monoamines. Particular examples include those having the formulas:

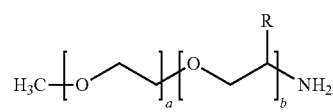

where R in each case is independently hydrogen, methyl or ethyl, and a and b independently are integers from about 1 to about 150;

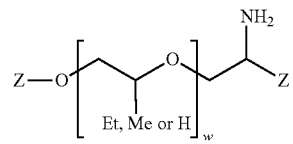

where each Z is independently a $C_1$-$C_{40}$ alkyl group or a $C_1$-$C_{40}$ alkyl phenol group and w is an integer from about 1 to about 100;

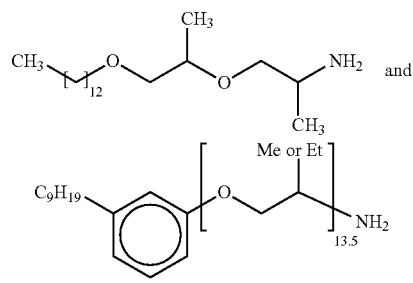

where Me is methyl and Et is ethyl. Such polyoxyalkylene monoamines included within the above formulas include the JEFFAMINE® M-600, M-1000, M-2005, M-2070, XTJ-435 and XTJ-436 amines.

Further commercially available polyoxyalkylene monoamines include the SURFONAMINE® B- and L-series amines which have the general structure:

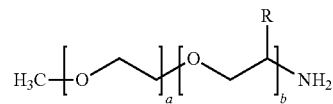

where R is methyl and a and b are integers such that the mole ratio of PO/EO in the compound ranges from about 9/1 to about 1/11. Thus, in some embodiments, R is methyl and the mole ratio of PO/EO ranges from about 9/1 to about 1/1 or from about 9/1 to about 4.5/1. In another embodiment, R is methyl and the mole ratio of PO/EO ranges from about 1/1 to about 1/11 or from about 1/3.3 to about 1/11 or from about 1/6.3 to about 1/11 or even from about 1/7 to about 1/11. While these compounds are methoxy terminated, the polyoxyalkylene monoamine can also be capped with other groups where the methyl group of the methoxy group is replaced with a higher hydrocarbon such as ethyl, propyl, butyl, phenyl, or benzyl.

The intermediate (a) can be prepared by contacting maleic anhydride and the polyoxyalkylene monoamine and allowing them to react at conventional temperatures. For example, the reaction may take place at a temperature ranging from about room temperature up to about 110° C. maximum, or from about 60° C. to about 100° C. Reaction times may vary from about 15 minutes to about 2 hours. Means for removing water of condensation can be employed and reduced pressures may be also desirable at lower reaction temperatures.

In some embodiments, the proportions of the maleic anhydride and polyoxyalkylene monoamine may be such that the moles of maleic anhydride are equal to or on average of from about 1 mole to about 3 moles less than the molar equivalents of amine groups in the polyalkylene monoamine.

The intermediate (a) is then reacted with a reactant to form the multifunctional additive compound of the present disclosure. According to one embodiment, the reactant may be an amine compound comprising a primary amine group or a secondary amine group. The amine compound may be aliphatic, cycloaliphatic, aromatic, or heterocyclic, including aliphatic-substituted cycloaliphatic, aliphatic-substituted aromatic, aliphatic-substituted heterocyclic, cycloaliphatic-substituted aliphatic, cycloaliphatic-substituted aromatic, cycloaliphatic-substituted heterocyclic, aromatic-substituted aliphatic, aromatic-substituted cycloaliphatic, aromatic-substituted heterocyclic, heterocyclic-substituted aliphatic, heterocyclic-substituted alicyclic, and heterocyclic-substituted aromatic amines and may also be saturated or unsaturated. If unsaturated, the amine will be free from acetylenic unsaturation (i.e., —C≡C—). The amine compound may also contain non-hydrocarbon substituents or groups as long as these groups do not significantly interfere with the reaction of the amine compound with the intermediate (a). Such non-hydrocarbon substituents or groups include lower alkoxy, lower alkyl mercapto, nitro, interrupting groups such as —O— and —S— (for e.g., as in such groups as —CH$_2$CH$_2$—X—CH$_2$CH$_2$— where X is —O— or —S—).

In one embodiment, the amine compound complies with the general formula (I) or (II):

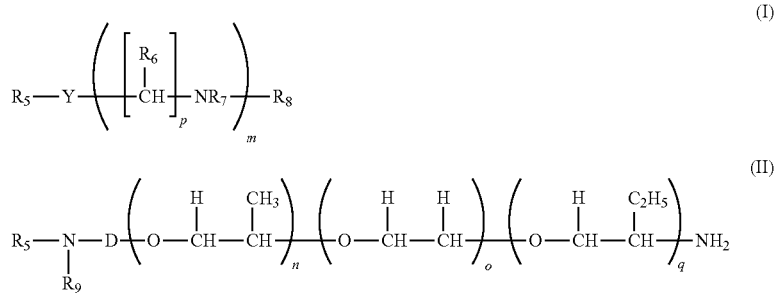

where $R_5$, $R_7$ and $R_8$, which can be the same or different, in each case represent a hydrogen atom or a hydrocarbon group having 1 carbon atom to 60 carbon atoms or in some embodiments 1 carbon atom to 48 carbon atoms, Y is —O— or an —NR$_9$— group in which R$_9$ represents a hydrogen atom or a hydrocarbon group having 1 carbon atom to 60 carbon atoms or in some embodiments 1 carbon atom to 48 carbon atoms, $R_5$ and $R_9$ being able to form together with the nitrogen atom to which they are linked a heterocycle, each of the $R_6$'s independently representing a hydrogen atom or a hydrocarbon group having 1 carbon atom to 4 carbon atoms, wherein when Y is —NR$_9$— p is an integer equal to or higher than 2, and in some embodiments between 2 and 10, and m is zero or an integer between 1 and 10 and wherein when Y is —O—, p is an integer equal to or higher than 1, and in some embodiments between 1 and 10, and m is an integer from 1 to 10, n, o and q are integers from 0 to 60 with the proviso that the sum of n+o+q is an integer from 1 to 60.

According to one embodiment, the amine is a compound of formula (I) and m is equal to zero and Y is —NR$_9$—. These monoamines comply with the general formula $R_5NR_9R_8$ and frequently use is made of those monoamines in which $R_8$ and $R_9$ represent a hydrogen atom and $R_5$ is an alkyl group having 1 carbon atom to 32 carbon atoms. As examples of these primary monoamines, reference can be made to methylamine, ethylamine, propylamine, butylamine, pentylamine, hexylamine, heptylamine, octylamine, nonylamine, decylamine, dodecylamine, tetradecylamine, hexadecylamine, octadecylamine, eicosylamine and docosylamine. It is also possible to use a mixture of primary monoamines. Use may also be made of secondary monoamines having a formula $R_5NHR_8$ where $R_5$ and $R_8$, which can be the same or different, in each case represent an alkyl group having 1 carbon atom to 32 carbon atoms or a mixture of secondary monoamines, such as for example, fatty amine fractions of formula $R_5NHR_8$, whose groups $R_5$ and $R_8$ are aliphatic hydrocarbon radicals in the $C_8$ $C_{10}$, $C_{12}$, $C_{14}$, $C_{16}$, $C_{18}$, $C_{20}$ and $C_{22}$ ranges.

It is also possible to use polyamines of formula (I), where $R_5$ is a hydrogen atom or a hydrocarbon group having 1 carbon atom to 32 carbon atoms, Y is —NR$_9$— in which $R_9$ is a hydrogen atom or a hydrocarbon group having 1 carbon atom to 32 carbon atoms, each of the $R_6$'s independently represent a hydrogen atom or a methyl group, p is an integer from 2 to 4 and m is an integer from 1 to 5.

Among the compounds of general formula (I), it is also possible to use those in which Y is —NR$_9$—, $R_5$, $R_6$ and $R_9$ each represent a hydrogen atom, p is equal to 2 and m is an integer from 1 to 5; or those in which $R_5$ represents a hydrocarbon group and in some embodiments having 5 carbon atoms to 24 carbon atoms, Y represents a —NR$_9$— group in which $R_9$ is a hydrogen atom, $R_6$ represents a hydrogen atom, p is an integer from 2 to 4, such as 3, and m is an integer from 1 to 5, such as 1.

The hydrocarbon groups $R_5$ and $R_9$ are normally straight or branched, alkenyl, alkyl, aryl, aryl-alkyl (aralkyl), alkyl-aryl (alkaryl) or cycloaliphatic groups. The groups $R_5$ and $R_9$ are in some embodiments straight or branched, alkyl or alkenyl groups. The hydrocarbon group $R_6$ may be a straight alkyl group, such as a methyl, ethyl, n-propyl or n-butyl group.

As specific compounds, examples include, but are not limited to, ethylene diamine, propylene diamine, triethylene tetramine, tripropylene tetramine, tetraethylene pentamine, trimethylene diamine, hexamethylene diamine, 2,2,4 and 2,4,4-trimethyl hexamethylene diamine, di(trimethylene)triamine, N-alkyl-1,3-diamino propane, e.g. N-1,3-dodecyldiaminopropane, N-1,3-tetradecyl diaminopropane, N-1,3-hexadecyldiaminopropane, N-1,3-octadecyldiaminopropane, N-1,3-eicosyldiamino propane and N-1,3-docosyldiaminopropane. Reference can also be made to N-alkyl dipropylene triamines, for example, N-hexadecyl dipropylene triamine, N-octadecyl dipropylene triamine, N-eicosyl dipropylene triamine and N-docosyl dipropylene triamine. Reference can also be made to N-1,3-alkenyldiaminopropane and N-alkenyl dipropylene triamines, for example, N-1,3octadecenyl diaminopropane, N-1,3-hexadecenyl diaminopropane, N-1,3-dodecylenyl diaminopropane, N-1,3-octadecadienyl diaminopropane and N-1,3-docosenyl diaminopropane. As examples of N,N-disubstituted diamines reference can be made to N,N-diethyl-1,2-diaminoethane, N, N-diisopropyl-1,2-diaminoethane, N,N-dibutyl-1,2-diaminoethane, N,N-diethyl-1,4-diaminobutane, N,Ndimethyl-1,3-diaminopropane, N,N-diethyl-1,3-diaminopropane, N,N-dioctyl-1,3-diaminopropane, N,N-didecyl-1,3-diaminopropane, N,N-didodecyl-1,3-diaminopropane, N,N-ditetradecyl-1,3-diaminopropane, N,N-dihexadecyl-1,3-diaminopropane, N,N-dioctadecyl-1,3-diaminopropane, N,N-didodecyldipropylene triamine, N,N-ditetradecyldipropylene triamine, N,N-dihexadecyldipropylene triamine, N,N-dioctadecyldipropylene, triamine, N-methyl, N-butyl, 1,2-diaminoethane, N-methyl-N-octyl-1,2-diaminoethane, N-ethyl, N-octyl-1,2-diaminoethane, N-methyl-N-decyl-1, 2-diaminoethane, N-methyl-N-dodecyl-1,3-diaminopropane, N-methyl-N-hexadecyl-1,3-diaminopropane and N-ethyl-N-octadecyl-1,3-diaminopropane.

Examples of ether amines include, but are not limited to, 2-methoxyethylamine, 3-methoxypropylamine, 4-methoxybutylamine, 3-ethoxypropylamine, 3-octyloxypropylamine, 3-decyloxypropylamine, 3-hexadecyloxypropylamine, 3-eicosyloxypropylamine, 3-docosyloxypropylamine, N-(3-octyloxypropyl)-1,3-diaminopropane, N-(3-decyloxypropyl)-1,3-diaminopropane, (2,4,6-trimethyldecyl) 3-oxypropylamine, N-(2,4,6-trimethyldecyl)3-oxypropyl) 1,3-diaminopropane, di-(2-methoxyethyl)-amine, di-(3-methoxy n-propyl)amine, di-(2-methoxy 2-methyl-ethyl)-amine, di-(3-ethoxy-npropyl)-amine, di-(n-3-propoxy-n-propyl)-amine, di-(n-3-butoxy-n-propyl)-amine, di-(n-3-pentoxy-n-propyl)-amine, di-(n-3-hexyloxy-n-propyl)-amine, di-(n-3-octyloxy-n-propyl)-amine, di-(n-3-nonyloxy-n-propyl)-amine and di-(n-3-decyloxy-n-propyl)-amine.

The amines of formula (II) may be those where $R_5$ and $R_9$ in each case represent a hydrogen atom and o is an integer from 1 to 60 and n and q are equal to zero, or o is an integer from 1 to 59, n is zero or an integer such that the sum of o+n is 1 to 59 and q is 0, or o is an integer from 1 to 59 and q is 0 or an integer such that the sum of o+q is 1 to 59 and n is 0, or o is an integer of from 1 to 59, n is an integer of from 1 to 59 and q is an integer of from 1 to 59 such that the sum of o+n+q is 3 to 60.

According to one particular embodiment, the amine compound is methylamine, ethylamine, dimethylamine, diethylamine, n-butylamine, di-n-butylamine, allylamine, isobutylamine, cocoamine, stearyl amine, laurylamine, methyllaurylamine, oleylamine, N-methyl-octylamine, dodecylamine, octadecylamine, 2-ethylhexylamine, di-(2-ethylhexyl)amine, methyl butylamine, 2-(cyclohexyl)-ethyl-amine, benzylamine, phenethyl-amine, 3-(furylpropyl) amine, cyclohexylamine, cyclopentylamine, cyclohexenylamine, cyclopentenylamine, N-ethyl-cyclohexylamine, dicyclohexylamine, propyl-substituted cyclohexylamine, phenyl-substituted cyclopentylamine, pyranyl-substituted cyclohexylamine, aniline, di(para-methylphenyl) amine, naphthylamine, N-(n-butyl)aniline, para-ethoxyaniline, para-dodecylaniline, cyclohexyl-substituted naphthylamine, thienyl-substituted aniline, ethylene diamine, triethylene tetramine, propylene diamine, trimethylene diamine, hexamethylene diamine, decamethylene diamine, octamethylene diamine, di(heptamethylene)triamine, tripropylene tetramine, tetraethylene pentamine, trimethylene diamine, pentaethylene hexamine, di-(trimethylene)triamine, N-(2-aminoethyl)piperazine, 1,4-bis(2-aminoethyl)piperazine, monoethanolamine, di-(3-hydroxypropyl)-amine, 3-hydroxybutyl-amine, 4-hydroxybutyl-amine, diethanolamine, N-(2-hydroxyethyl)-cyclohexylamine, 3-hydroxycyclopentylamine, para-hydroxyaniline, N-hydroxyethyl piperazine, methylethanolamine, diisopropanolamine, ethylpropanolamine, methyldipropanolamine, methyldiethanolamine, ethyldiethanolamine, propyldiethanolamine, isopropyldiethanolamine, methyldiisopropanolamine, ethyldiisopropanolamine, propyldiisopropanolamine, diethylethanolamine, dimethylethanolamine, dipropylethanolamine, 2-methoxyethylamine, 3-methoxypropylamine, 4-methoxybutylamine, 3-ethoxypropylamine, 3-octyloxypropylamine, 3-decyloxypropylamine, 3-hexadecyloxypropylamine, 3-eicosyloxypropylamine, 3-docosyloxypropylamine, N-(3-octyloxypropyl)-1,3-diaminopropane, N-(3-decyloxypropyl)-1,3-diaminopropane, (2,4,6-trimethyldecyl) 3-oxypropylamine, N-[(2,4,6-trimethyldecyl)3-oxypropyl]1,3-diaminopropane, di-(2-methoxyethyl)-amine, di-(3-methoxy n-propyl)amine, di-(2-methoxy 2-methyl-ethyl)-amine, di-(3-ethoxy-n-propyl)-amine, di-(n-3-propoxy-n-propyl)-amine, di-(n-3-butoxy-n-propyl)-amine, di-(n-3-pentoxy-n-propyl)-amine, di-(n-3-hexyloxy-n-propyl)-amine, di-(n-3-octyloxy-n-propyl)-amine, di-(n-3-nonyloxy-n-propyl)-amine, di-(n-3-decyloxy-n-propyl)-amine and mixtures thereof.

The additive compound of the present invention can be prepared by reacting the intermediate (a) with the amine compound (b) at a temperature of from about 0° C. to about 300° C. In one embodiment, the temperature for the reaction is from about 10° C. to about 150° C. or from about 50° C. to about 120° C. or from about 80° C. to about 110° C. or from about 95° C. to about 105° C. The reaction can be carried out for a time period that is sufficient to complete the reaction. This time period may be from about 10 minutes to about 24 hours or from about 30 minutes to about 12 hours or from about 30 minutes to about 2 hours. The reaction can optionally be carried out neat or in the presence of solvent. The reaction can be conducted either under reduced pressure, atmospheric pressure or superatmospheric pressure in an inert atmosphere such as, for example, nitrogen, helium, neon, xenon, argon, mixtures thereof and the like. The amount of the amine compound (b) used in the reaction with the intermediate (a) may be within a molar ratio of the amine compound (b) to maleic anhydride used in forming the intermediate (a) of about 3:1 to about 1:3 or from about 2:1 to about 1:2 or from about 1.5:1 to about 1:1.5 or from about 1:1.

According to one embodiment, the additive in solution, depending on pH of the solution, may have a formula according to:

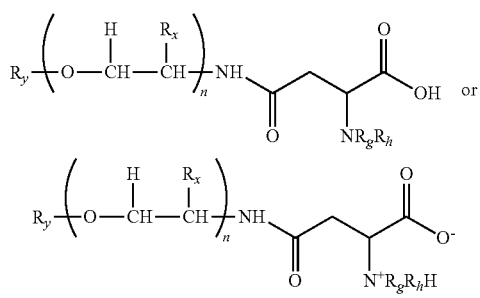

where $R_y$ is an alkyl group having 1 to 32 carbon atoms, n is an integer from 2 to 30, each $R_x$ is independently hydrogen, methyl or ethyl and $R_g$ and $R_h$ are independently hydrogen or an alkyl group having 1 to 32 carbon atoms.

According to another embodiment, there is provided a packaged product comprising: a) a container having at least an outlet; and b) the additive compound of the present disclosure.

According to one embodiment, the packaged product of the present disclosure comprises a container having a closure means, such as a lid, cover, cap, or plug to seal the container. In another embodiment, the sealed container also has a nozzle or pour spout. The sealed container may have the shape of a cylinder, oval, round, rectangle, canister, tub, square or jug and contains the composition of the present disclosure.

In yet another embodiment, the container may be made from any material, such as steel, glass, aluminum, cardboard, tin-plate, plastics including, but not limited to, high density polyethylene (HDPE), polypropylene (PP), polyvinyl chloride (PVC), polyethylene terephthalate (PET), oriented polypropylene (OPP), polyethylene (PE) or polyamide and including mixtures, laminates or other combinations of these.

The additive compound of the present disclosure may be useful in a variety of applications, such as in fuel deposit control agents, corrosion inhibition, detergency, metalworking fluids, mining reagents, emulsifiers, in fuel or lubricant compositions, surfactant manufacture and for dispersing pigments or asphalt/cement.

Thus, in one embodiment, there is provided a composition comprising the additive compound of the present disclosure and at least one of a solvent, a surfactant or an auxiliary. The amount of the additive compound contained in the composition may range from about 0.0001% by weight up to less than 50% by weight, based on the total weight of the composition.

According to one embodiment the solvent is water, and in some embodiments, de-ionized water. In other embodiments a different solvent may be used in addition to or in place of water. Examples of such solvents include, but are not limited to, hydrocarbons (e.g. pentane or hexane), halocarbons (e.g. Freon 113), ethers (e.g. ethylether ($Et_2O$), tetrahydrofuran ("THF") or diglyme (diethyleneglycol dimethyl ether)), nitriles (e.g. $CH_3CN$), or aromatic compounds (e.g. benzotrifluoride). Still further exemplary solvents include lactates, pyruvates, and diols. Solvents can also include, but are not limited to, acetone, 1,4-dioxane, 1,3-dioxolane, ethyl acetate, cyclohexanone, acetone, 1-methyl-2-pyrodidianone (NMP), and methyl ethyl ketone. Other solvents, include dimethylformamide, dimethylacetamide, N-methyl pyrrolidone, ethylene carbonate, propylene carbonate, glycerol and derivatives, naphthalene and substituted versions, acetic acid anhydride, propionic acid and propionic acid anhydride, dimethyl sulfone, benzophenone, diphenyl sulfone, phenol, m-cresol, dimethyl sulfoxide, diphenyl ether, terphenyl, and the like. Still further solvents include propylene glycol propyl ether (PGPE), 3-heptanol, 2-methyl-1-pentanol, 5-methyl-2-hexanol, 3-hexanol, 2-heptanol, 2-hexanol, 2,3-dimethyl-3-pentanol, propylene glycol methyl ether acetate (PGMEA), ethylene glycol, isopropyl alcohol (IPA), n-butyl ether, propylene glycol n-butyl ether (PGBE), 1-butoxy-2-propanol, 2-methyl-3-pentanol, 2-methoxyethyl acetate, 2-butoxyethanol, 2-ethoxyethyl acetoacetate, 1-pentanol, and propylene glycol methyl ether. The solvents enumerated above may be used alone or in combination.

The composition may include a surfactant. Surfactants useful in the composition of the present disclosure are well known and include anionic, nonionic, cationic and amphoteric compounds. Combinations of more than one such compound may be used in the composition.

Anionic surfactant compounds which may be used include, but are not limited to, alkyl sulfates, alkyl benzene sulfonates, α-olefin sulfonates, alkyl taurates, alkyl sacrosinates, alkyl diphenyloxide disulfonates, alkyl naphthalene sulfonates, alkyl ether sulfates, alkyl ether sulfonates, sulfo-succinates, and other anionic surfactants as known for use in, for example, performance chemical formulations, including linear $C_{8-16}$ alkyl sulfates, $C_{8-16}$ alkyl sulfonates, $C_{8-16}$ alkyl benzene sulfonates and $C_{8-16}$ alkyl diphenyloxide disulfonates, decyl sulfophenoxy benzene/oxybis decyl benzene sulfonic acid disodium salt, and sodium octane sulfonate, sodium dodecyl sulfonate, sodium lauryl sulfate, and combinations of the foregoing. These surfactants are typically available as the alkali metal, alkaline earth and ammonium salts thereof.

Nonionic surfactant compounds which may be used include, but are not limited to, alkoxylates, N-substituted fatty acid amides, amine oxides, esters, sugar-based surfactants, polymeric surfactants, and mixtures thereof. Examples of alkoxylates are compounds such as non-aromatic alcohols, amines, amides, fatty acids or fatty acid esters which have been alkoxylated with 1 to 50 equivalents. Ethylene oxide and/or propylene oxide may be employed for the alkoxylation, usually ethylene oxide.

Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters. Examples of polymeric surfactants are homo- or copolymers of vinylpyrolidone, vinylalcohols, or vinylacetate.

Cationic surfactant compounds may also be used including quaternary surfactants, for example quaternary ammonium compounds with one or two hydrophobic groups, or salts of long-chain primary amines.

Amphoteric surfactant compounds which may be used include, but are not limited to, betaines, alkyl imidazolines, cocoamphopropionates, disodium cocoamphodipropionate (also known as cocoimidazoline carboxylate), or combinations thereof.

Known auxiliaries may also be added to the composition depending upon the application. These auxiliaries may include, but are not limited to, colorants, pigments, enzymes, wetting agents, antifoaming agents, buffering agents, pH adjusting agents, thickening agents, emulsifiers, anti-streaking agents, builders, chelating or sequestering agents, hydrotopes, anti-microbial agents, perfumes, herbicides, pesticides, fungicides, anti-oxidants, anti-wear additives, friction modifiers, viscosity index improvers, pour point depressants, corrosion inhibitors, solid carriers or fillers, protective colloids, adhesion agents, humectants, repellents, attractants, feeding stimulants, compatibilizers, bactericides, anti-freezing agents, crystallization inhibitors, tackifiers, binders, preservatives, clarifiers, fertilizers, UV stabilizers, salts, weighting agents, gravel particulates, gases, crosslinkers, thermodynamic hydrate inhibitors, kinetic hydrate inhibitors, clay stabilizing agents and mixtures thereof.

According to one embodiment there is provided a performance chemical formulation comprising the composition of the present disclosure where the additive compound is present in the performance chemical formulation in an amount ranging from about 0.001% by weight to about 40% by weight, based on the total weight of the performance chemical formulation. In another embodiment, there is provided a performance chemical formulation comprising the composition where the additive compound is present in the performance chemical formulation in an amount ranging from about 0.01% by weight to about 30% by weight, based on the total weight of the performance chemical formulation. In still another embodiment, there is provided a performance chemical formulation comprising the composition where the additive compound is present in the performance chemical formulation in an amount ranging from about 0.05% by weight to about 20% by weight, based on the total weight of the performance chemical formulation. In yet still another embodiment, there is provided a performance chemical formulation comprising the composition where the additive compound is present in the performance chemical formulation in an amount ranging from about 0.5% by weight to about 15% by weight, or from about 1% by weight to about 10% by weight, based on the total weight of the performance chemical formulation.

Accordingly, in still another embodiment there is provided a personal care formulation comprising the composition where the additive compound is present in the personal care formulation in an amount ranging from about 0.001% by weight to about 40% by weight, based on the total weight of the performance chemical formulation. In another embodiment, there is provided a performance chemical formulation comprising the composition where the additive compound is present in the personal care formulation in an amount ranging from about 0.01% by weight to about 30% by weight, based on the total weight of the personal care formulation. In still another embodiment, there is provided a personal care formulation comprising the composition where the additive compound is present in the personal care formulation in an amount ranging from about 0.05% by weight to about 20% by weight, based on the total weight of the personal care formulation. In yet still another embodiment, there is provided a personal care formulation comprising the composition where the additive compound is present in the personal care formulation in an amount ranging from about 0.5% by weight to about 15% by weight or about 1% by weight to about 10% by weight, based on the total weight of the personal care formulation.

According another embodiment, a concentrated composition comprising the additive of the present disclosure is provided that may be further diluted in water and/or other solvent(s) to form an aqueous or non-aqueous solution. A concentrated composition of the present disclosure or "concentrate" allows one to dilute the concentrate to the desired strength and pH. A concentrate also permits longer shelf life and easier shipping and storage. Thus, in one embodiment there is provided a concentrate composition containing the additive of the present disclosure and water and/or other solvent and optionally one or more auxiliaries described above. For the concentrate, the amount of water (and in some embodiments, de-ionized water) and/or solvent may, for instance, be from about 0.5% by weight to about 50% by weight, based on the total weight of the concentrate. Accordingly, the amount of the additive compound (and optional auxiliaries if present) contained in the concentrate may range from about 50% by weight up to 99.5% by weight, based on the total weight of the concentrate. As noted above, the concentrate may be further diluted with water, and in some embodiments, de-ionized water, and/or solvent to form the aqueous or non-aqueous solution In one particular embodiment, the additive compound is useful in a corrosion inhibiting composition. The corrosion inhibiting composition is suitable for use in connection with metallic components used in the manufacture of commercial equipment associated with aqueous or non-aqueous systems that require corrosion protection. "Aqueous System" refers to any system containing metallic components which contain or are in contact with aqueous fluids on a periodic or continuous basis. The term "aqueous fluids' refers to fluids containing 5% by weight or more of water and includes water-based fluids. "Water based fluids" refer to fluids containing a minimum of 40% by weight water, the remainder being suspended and/or dissolved solids and compounds that are soluble in water. "Non-aqueous system" refers to any system containing metallic components which contain or are in contact with non-aqueous fluids on a periodic or continuous basis. Non-aqueous fluids may be miscible or immiscible in water, such as hydrocarbon fuels. Typical aqueous or non-aqueous systems may include, for example, recirculating cooling units, open recirculating cooling units that utilize evaporation as a source of cooling, closed loop cooling units, heat exchanger units, reactors, equipment used for storing and handling liquids, boilers and related steam generating units, radiators, flash evaporating units, refrigeration units, reverse osmosis equipment, gas scrubbing units, blast furnaces, paper and pulp processing equipment, sugar evaporating units, steam power plants, geothermal units, nuclear cooling units, water treatment units, food and beverage processing equipment, pool recirculating units, mining circuits, closed loop heating units, machining fluids used in operations such as for example drilling, boring, milling, reaming, drawing, broaching, turning, cutting, sewing, grinding, thread cutting, shaping, spinning and rolling, hydraulic fluids, cooling fluids, oil production units and drilling fluids. Typical examples of aqueous fluids include freshwater, brackish water, sea water, waste water, mixtures of water and salts (known as brines), mixtures of water and alcohols such as methanol, ethanol and ethylene glycol, mixtures of water and acids such as mineral acids, mixtures of water and bases such as caustic and combinations thereof. Aqueous and non-aqueous systems treated using the corrosion inhibiting compositions of this disclosure may contain dissolved oxygen or may contain no oxygen. The aqueous and non-aqueous systems may contain other dissolved gases such as, for example, carbon dioxide, ammonia and hydrogen sulfide.

Thus, according to one embodiment, there is provided a corrosion inhibiting composition comprising the additive compound and an aqueous fluid. In another embodiment, there is provided a corrosion inhibiting composition comprising the additive compound and a non-aqueous fluid.

According to one embodiment, the metallic components that may come in contact with the aqueous or non-aqueous systems are processed from any metal for which corrosion and/or scaling can be prevented. Typical examples of metals requiring corrosion protection are copper, copper alloys, aluminum, aluminum alloys, ferrous metals, such as iron, steels such as low carbon steel, chromium steel and stainless steel, iron alloys and combinations thereof.

The corrosion inhibiting compositions of the present disclosure are effective in highly acidic or basic aqueous systems, namely at a pH between 0.5 and 14. In some embodiments it is preferred that the corrosion inhibiting compositions are added to the aqueous or non-aqueous systems at a pH between 6 and 10.

The corrosion inhibiting composition may be added to the aqueous system in an amount such that the additive compound of the present disclosure is present in the aqueous system at active amounts ranging between about 0.1 ppm to about 50,000 ppm (0.00001 to 5% by weight), or between about 1 ppm to about 10,000 ppm, or between about 50 ppm to about 5000 ppm or between about 100 ppm to about 1000 ppm, based on the weight of the aqueous system.

The corrosion inhibiting composition is also useful as a corrosion inhibitor for metallic components that come into contact with non-aqueous systems and fluids such as a hydrocarbon fuel. The hydrocarbon fuel may be a biofuel or motor fuel composition comprising a mixture of hydrocarbons boiling in the gasoline boiling range. This fuel may consist of straight chain or branched-chain paraffins, cycloparaffins, olefins, and aromatic hydrocarbons and any mixture of these. The fuel can be derived from straight-run naphtha, polymer gasoline, natural gasoline or from catalytically cracked or thermally cracked hydrocarbon and catalytically reformed stocks and boils in the range from about 80° F. to 450° F. The composition and the octane level of the fuel are not critical. Any conventional motor fuel base can be employed in the practice of this invention including gasolines. The gasoline containing the additive compound may also contain conventional auxiliaries such as antiknock compounds, antioxidants, metal deactivators, corrosion inhibitors besides the additive compound of the present disclosure, anti-icing agents, dehazer agents, detergents and the like.

According to another embodiment, the corrosion inhibiting composition, in addition to preventing corrosion of metallic components, may also provide surprisingly effective carburetor detergency.

In general, the additive may be added to the hydrocarbon fuel or gasoline in a minor amount, i.e., an amount effective to provide corrosion inhibition or carburetor detergency or both to the hydrocarbon fuel gasoline. The additive may be effective in an amount ranging from about 0.0002-0.2% by weight, based on the total weight of the hydrocarbon fuel or gasoline. In some embodiments, an amount ranging from about 0.001-0.01% by weight, based on the total weight of the hydrocarbon fuel or gasoline, may be preferred, the latter amounts corresponding to about 3 and 30 PTB (pounds of additive per 1000 barrels of hydrocarbon fuel or gasoline) respectively.

The present disclosure will now be further described with reference to the following non-limiting examples.

EXAMPLES

Examples 1-3. Preparation of Inventive Multifunctional Additives 196 grams of maleic anhydride was melted in an oven at a temperature of 70° C. The melted anhydride was then charged into a 5-L three neck flask and held at a temperature of 60° C. Under mild agitation, 2000 grams of a polyoxyalkylene monoamine (JEFFAMINE® XTJ-436 amine) was added into the reactor and the mixture was allowed to react at a temperature of about 60° C. for 30 minutes. 600 grams of 2-ethylhexane solvent was added to control the viscosity of the mixture. 204 grams of dimethylaminopropylamine (DMAPA) was then added to the reactor and the temperature of the reactor was increased to 100° C. This mixture was then allowed to react for 2 hours before being cooled. The product that was obtained, a light yellow liquid, was then collected and identified as Example 1.

98 grams of maleic anhydride was melted in an oven at a temperature of 70° C. The melted anhydride was then charged into a 5-L three neck flask and held at a temperature of 60° C. Under mild agitation, 1837 grams of a polyoxyalkylene monoamine that had been made by the amination of a polyol produced from the reaction of a propylene oxide (PO)/butylene oxide (BO) mixture and dodecyl phenol (DDP) was then added into the reactor and the mixture was allowed to react at a temperature of about 60° C. for 30 minutes. 102 grams of DMAPA was then added to the reactor and the temperature of the reactor was increased to 100° C. The mixture was allowed to react for 2 hours before being cooled. The product that was obtained, a light yellow liquid was collected and identified as Example 2.

49 grams of maleic anhydride was melted in an oven at a temperature of 70° C. The melted anhydride was then charged into a 5-L three neck flask and held at a temperature of 60° C. Under mild agitation, 500 grams of a polyoxyalkylene monoamine (JEFFAMINE® XTJ-436 amine) was added to the reactor the mixture was allowed to react at a temperature of about 60° C. for 30 minutes. 145 grams of 2-ethylhexane solvent was added to control the viscosity of the mixture. 30.5 grams of monoethanolamine (MEA) was then added into the reactor and the temperature of the reactor was increased to 100° C. The mixture was allowed to react for 2 hours before being cooled. The product that was obtained, a light yellow liquid, was then collected and identified as Example 3.

Example 4. Use of the Additives of the Present Disclosure as Corrosion Inhibitors A. Corrosion Inhibitor Evaluation Procedure:
1) Carbon steel coupons were sanded by sandpaper before use.
2) Half of the carbon steel coupon was inserted into the tested liquid.
3) The temperature of the tested liquid was then maintained at 30° C. for 5 hours under agitation.
4) The carbon steel coupon was removed from the tested liquid and the amount of corrosion/rust on the carbon steel coupon was evaluated as pass/fail, (i.e. at least 50% of the coupon exposed to the tested liquid exhibited corrosion/rust.

| Liquid | Result |
| --- | --- |
| Group II oil/deionized water* | Fail |
| Group II oil/deionized water* + 500 ppm of Example 1 | Pass |
| Group II oil/salt water* | Fail |
| Group II oil/salt water* + 500 ppm of Example 1 | Pass |
| Gasoline/salt water* | Fail |
| Gasoline/salt water* + 500 ppm of Example 1 | Pass |

| Liquid | Result |
| --- | --- |
| Gasoline/salt water* + 500 ppm of Example 2 | Pass |
| Gasoline/salt water* + 500 ppm of Example 3 | Pass |
| Gasoline/salt water* + 100 ppm of Example1 | Pass |
| Gasoline/salt water* + 100 ppm of Example 2 | Pass |
| Gasoline/salt water* + 100 ppm of Example3 | Pass |

*10/1 weight ratio

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. An additive compound obtained by the reaction of: (a) an intermediate formed from the reaction of maleic anhydride and a polyoxyalkylene monoamine; and (b) an amine compound comprising a primary amine group and/or a secondary amine group having the formula (I):

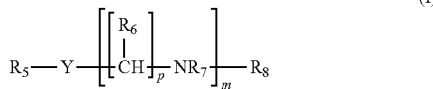

wherein $R_5$, $R_7$ and $R_8$, which can be the same or different, in each case are a hydrogen atom or a hydrocarbon group having 1 carbon atom to 60 carbon atoms, Y is —O—, p is an integer equal to or higher than 1 and m is an integer between 1 and 10, and each $R_6$ is independently a hydrogen atom or a hydrocarbon group having 1 carbon atom to 4 carbon atoms.

2. The additive compound of claim 1, wherein p is an integer between 1 and 10, $R_5$, $R_7$ and $R_8$ are hydrogen and $R_6$ is hydrogen or methyl.

3. The additive compound of claim 1, wherein the polyoxyalkylene monoamine is a compound having a formula:

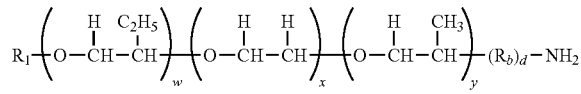

where $R_1$ is hydrogen, a $C_1$ to $C_{20}$ alkyl group or a $C_6$ aryl group optionally substituted with one or more $C_1$ to $C_{10}$ alkyl groups; w, x, and y are each independently an integer between zero to about 100, subject to the proviso that w+x+y is greater than two; d is 0 or 1; and, $R_b$ is a $C_1$ to $C_{10}$ alkyl group.

4. A method of forming an additive compound comprising reacting (a) an intermediate formed from the reaction of maleic anhydride and a polyoxyalkylene monoamine with (b) an amine compound comprising a primary amine group and/or a secondary amine group having the formula (I):

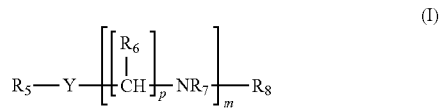

wherein $R_5$, $R_7$ and $R_8$, which can be the same or different, in each case are a hydrogen atom or a hydrocarbon group having 1 carbon atom to 60 carbon atoms, Y is —O—, p is an integer equal to or higher than 1 and m is an integer between 1 and 10, and each $R_6$ is independently a hydrogen atom or a hydrocarbon group having 1 carbon atom to 4 carbon atoms.

5. The method of claim 4, wherein an amount of the amine compound (b) used in the reaction with the intermediate (a) is within a molar ratio of the amine compound (b) to maleic anhydride used in forming the intermediate (a) of about 1.5:1 to about 1:1.5.

6. A composition comprising the additive compound of claim 1 and at least one of a solvent, a surfactant or an auxiliary.

7. The composition of claim 6, wherein the additive compound is present in an amount of from 0.0001% by weight to less than 50% by weight, based on the total weight of the composition.

8. A performance chemical formulation comprising the composition of claim 6, wherein the additive compound is present in the performance chemical formulation in an amount ranging from about 0.001% by weight to about 40% by weight, based on the total weight of the performance chemical formulation.

9. A personal care formulation comprising the composition of claim 6, wherein the additive compound is present in the performance chemical formulation in an amount ranging from about 0.001% by weight to about 40% by weight, based on the total weight of the personal care formulation.

10. A corrosion inhibiting composition comprising the additive of claim 1 and an aqueous fluid.

11. The corrosion inhibiting composition of claim 10, wherein the aqueous fluid is selected from freshwater, brackish water, sea water, waste water, a mixture of water and salts, a mixture of water and alcohol, a mixture of water and acid, a mixture of water and caustic and a combination thereof.

12. A corrosion inhibiting composition comprising the additive of claim 1 and a non-aqueous fluid.

13. The corrosion inhibiting composition of claim 12, wherein the non-aqueous fluid is a hydrocarbon fuel.

* * * * *